United States Patent [19]
Mackles et al.

[11] Patent Number: 5,811,131
[45] Date of Patent: Sep. 22, 1998

[54] TASTELESS FORMS OF BASIC DRUGS PREPARED BY ADSORPTION IN SITU

[76] Inventors: Leonard Mackles, 311 E. 23rd St., New York, N.Y. 10010; Leonard Chavkin, 701 Warren Glen Rd., Bloomsbury, N.J. 08804

[21] Appl. No.: 802,365

[22] Filed: Feb. 19, 1997

[51] Int. Cl.⁶ .......................... A61K 33/06; A61K 33/12; A61K 31/445; A61K 31/135
[52] U.S. Cl. .......................... 424/683; 424/666; 424/682; 424/684; 424/692; 514/327; 514/574; 514/648; 514/653; 514/974
[58] Field of Search ..................... 514/327, 648, 514/653, 974, 574; 424/666, 692, 683, 684, 682

[56] References Cited

FOREIGN PATENT DOCUMENTS 9420074  9/1994  WIPO.

*Primary Examiner*—Phyllis G. Spivack
*Attorney, Agent, or Firm*—Omri M. Behr, Esq.

[57] ABSTRACT

The present invention provides tasteless liquid compositions for oral ingestion of pharmacologically active agents having basic moieties, wherein the compositions contain the basic pharmacologically active agent in the form of a salt of a pharmacologically acceptable organic acid, a silicate adsorbent and a sufficient amount of water to suspend the foregoing components. There are also provided methods of making these compositions.

15 Claims, No Drawings

TASTELESS FORMS OF BASIC DRUGS PREPARED BY ADSORPTION IN SITU

FIELD OF THE INVENTION

Tasteless liquid compositions of basic pharmacologically active agents.

DISCUSSION OF THE PRIOR ART

It is frequently desirable to prepare liquid forms of basic drugs, such as syrups or elixirs, particularly for administration to children or for anyone who experiences difficulty in swallowing solid dosage forms such as tablets or capsules.

Many such basic drugs are common to a variety of therapeutic categories such as antihistamines, antitussives, decongestants, H2 antagonists, vitamins such as thiamine, and many others with basic moieties as part of their molecular structure.

Without exception these medicaments are bad tasting, either bitter, anesthetic, or irritating to the oral mucosa.

Traditional methods for preparing liquid forms of these ingredients have involved using high concentrations of flavors and sweeteners in an attempt to mask their bad tastes. These methods offer only a partial solution to the problem The pharmaceutical formulators' art also recites methods for taste masking of bitter drugs by the preparation of less soluble versions of these drugs by coating them through various methods of micro encapsulation.

Thus, for example, it is possible to purchase coated Acetaminophen in which the powdered drug is micro encapsulated by 15% ethyl cellulose. Since its solubility is thereby reduced, its bitter irritating taste is similarly reduced. However, the product still is characteristically bitter and irritating when ingested. Micro encapsulation techniques also, by the reduced-solubility effect on the drug they produce, introduce the problem of reduced rate or completeness of the bioavailability of the drug.

Also, the micro encapsulation process is a separate step that must precede the preparation of the final dosage form thus adding significantly to the cost of the product.

Another technique for taste masking drugs is the preparation of adsorbates. This involves preparing a solution of the drug and mixing it with an insoluble powder that will adsorb the drug, removing the solvent, drying the resultant powder, and then using this dried adsorbate in the preparation of the final dosage form.

An illustrative example is the marketed product Dextromethorphan adsorbate in which 10% Dextromethorphan is adsorbed on 90% magnesium trisilicate. This product still has the characteristic bitterness of the drug but to a much lesser degree than that of the untreated form, i.e. Dextromethorphan Hydrobromide.

And since the preparation of the adsorbate involves a separate production process, the cost of using the adsorbate is significantly higher than that of using the hydrobromide.

Surprisingly, we have discovered that it is possible to mask the taste of bitter basic drugs in-situ, that is during the preparation of the final liquid dosage form. In addition to the cost saving this single step technique embodies, we have found that it is possible to completely mask the taste of basic drugs, eliminating rather than reducing their offensive nature.

SUMMARY OF THE INVENTION

The present invention provides a tasteless liquid composition for the oral ingestion of pharmacologically active agents having basic moieties, which contains the basic pharmacologically active agent in the form of a salt of a pharmacologically acceptable organic acid, a silicate adsorbent suitably selected from the group consisting of magnesium silicate, calcium silicate, magnesium aluminum silicate, and magnesium trisilicate, in a weight excess of suitably from about 5 to about 10 times the weight of the said salt, and a sufficient amount of water to suspend the foregoing components.

The novel compositions of the present invention may be made from the said pharmacologically active material in the form of a salt of an organic acid where it is available, from the basic form of the active material or from the form of the active material as the salt of an inorganic acid.

It is the last form which is generally the most readily available commercially. There is initially utilized with an aqueous solution of the said pharmacologically active material in the form of a salt of an inorganic acid in water. To this solution is added magnesium oxide or hydroxide in an equimolar or small excess amount, suitably equal to 1 to 1.2 equivalents of said inorganic acid to form in situ, the basic form of said pharmacologically active material. Then there is added a water soluble pharmacologically acceptable organic acid similarly in an equimolar or small excess amount, suitably equal to 1 to 1.2 equivalents of said pharmacologically active agent having basic moieties. There after there is added a silicate adsorbent, in a weight excess.

The mode of preparation may be varied, depending on the starting material. Where the starting material is the organic salt itself, the steps of basification and addition of an organic acid are omitted. Similarly if the starting material is the basic form itself, the step of basification is omitted.

DESCRIPTION OF THE PREFERRED EMBODIMENTS

In the preferred mode of preparing the novel tasteless composition of the present invention there are several steps. First the drug is dispersed in the formula weight of water. Some such drugs are available as the base but in many cases the base is either not stable or cannot be crystallized in the synthesis involved in its production. If it is a salt such as a hydrochloride, hydrobromide or sulfate, the salt is dispersed or dissolved in the formula weight of water. The mixture is then heated to 50°–90° C., suitably to 70°–80° C. and an approximately equimolar amount of a mild inorganic base is added and mixed thoroughly. The most suitable bases are magnesium oxide or magnesium hydroxide. This mixture is then stirred rapidly, suitably for from about 10 to about 30 minutes, usually for about fifteen minutes. During this time the salt is neutralized and the drug is converted to its basic form.

If the drug is available as the base, all that is required is that it be dispersed in the formula weight of water at the above temperatures as the first step.

The next step involves the addition of an approximately equimolar amount of a water soluble pharmacologically acceptable organic acid. citric, tartaric, malic, fumaric, and succinic acids are suitable, citric being preferred.

This mixture is again heated in the above temperature range for a similar time, during which time an organic acid salt (e.g. citrate) is formed.

Next, the adsorbent is added to the mixture and mixed well at the same temperature range. This mixture no longer exhibits the bitter taste of the drug which is masked completely.

Suitable adsorbents are magnesium aluminum silicate (Veegum®) or various forms of magnesium trisilicate or magnesium and/or calcium silicates (Celcate®). Effective amounts are in the range of five to ten times the weight of the drug.

Finally the other formula ingredients are added, the mixture is made homogeneous by stirring or homogenizing and the process is complete. The liquid dosage form is ready for packaging.

These other formula ingredients typically will include flavors, sweeteners, viscosity builders, preservatives, suspending agents and colors. These are added after the foregoing steps, and generally at lower temperatures. For example flavors should be added below 50° C. Of course, these additives will vary and will be chosen by those skilled in the art to achieve the final appearance, stability and taste characteristics desired.

EXAMPLES

Example 1

Loperamide Suspension
1 mg. per 5 ml. teaspoonful

| | |
|---|---|
| 1. Loperamide HCl | 0.02 |
| 2. Magnesium Hydroxide | 0.10 |
| 3. Citric Acid | 0.10 |
| 4. Veegum F | 3.00 |
| 5. CMC 7HF | 0.50 |
| 6. Titanium Dioxide | 1.00 |
| 7. Potassium Benzoate | 0.10 |
| 8. Potassium Sorbate | 0.30 |
| 9. Sorbitol | 10.00 |
| 10. Sucrose | 20.00 |
| 11. Flavors | 0.30 |
| 12. Water qs to | 100.00 |

The composition is formed in the following manner: In a suitable vessel 1,2, and 12 are mixed and heated to 80° C. with rapid mixing for ten minutes. Then 3 is added and mixing continued for an additional ten minutes. Thereafter 4 is added and mixed for five minutes until taste of Loperamide is completely absent. 5 is dusted in with rapid stirring to disperse with no lumps. Finally 6,7,8,9,10 are added and mixed to disperse and dissolve. The mixture is cooled to 50° or below and 11 added. Finally more citric acid is added to adjust the pH to 4.0 to 4.5

In accordance with the above procedure, but starting with any other inorganic salt of a basic pharmacologically active agent, the corresponding tasteless product is obtained.

Example 2

Antihistamine Suspension

| | % w/w |
|---|---|
| 1. Diphenhydramine Citrate | 1.0 |
| 2. Magnesium Trisilicate | 5.0 |
| 3. Magnesium Aluminum Silicate | 3.0 |
| 4. CMC 7HF | 0.5 |
| 5. Titanium Dioxide | 1.0 |
| 6. Methyl Paraben | 0.1 |
| 7. Propyl Paraben | 0.05 |
| 8. Glycerin | 15.0 |
| 9. Sucrose | 25.0 |
| 10. Flavors | 0.5 |
| 11. Water qs to | 100.0 |

The composition is formed in the following manner: In a suitable vessel 1 and 11 are mixed and heated to 70° C. 2 and 3 are added slowly with rapid mixing to disperse, mixing is continued until bitterness is no longer evident. 4 is slowly dusted in with rapid mixing. 5, 6, 7, 8 and 9 are added and mixed to disperse and dissolve. The mixture is cooled to 50° C. or below and 10 added and homogenized.

In accordance with the above procedure, but starting with any other organic salt of a basic pharmacologically active agent, the corresponding tasteless product is obtained.

Example 3

Decongestant Suspension

| | % w/w |
|---|---|
| 1. Phenylpropanolamine Base | 0.5 |
| 2. Citric Acid | 0.2 |
| 3. Magnesium Aluminum Silicate | 5.0 |
| 4. CMC 7HF | 0.5 |
| 5. Titanium Dioxide | 1.0 |
| 6. Methyl Paraben | 0.1 |
| 7. Propyl Paraben | 0.05 |
| 8. Glycerin | 15.0 |
| 9. Sucrose | 25.0 |
| 10. Flavors | 0.5 |
| 11. Water qs to | 100.0 |

The composition is formed in the following manner: In a suitable vessel 1, 2 and 11 are mixed and heated to 70° C. until dissolved. Then 3 is added and mixed for five minutes until bitter taste is completely absent. 4 is dusted in with rapid mixing. Finally 5, 6, 7, 8 and 9 are added and mixed to disperse and dissolve. The mixture is cooled to 50° C. and flavorants added and the mixture homogenized.

In accordance with the above procedure, but starting with any other basic pharmacologically active agent, the corresponding tasteless product is obtained.

We claim:

1. A tasteless liquid composition for the oral ingestion of pharmacologically active agents having basic moieties comprising:
   a) a basic pharmacologically active agent in the form of a salt of a pharmaceutically acceptable organic acid selected from the group consisting of citric, tartaric, malic, fumaric and succinic acids,
   b) a silicate adsorbent selected from the group consisting of magnesium silicate, calcium silicate, magnesium aluminum silicate, and magnesium trisilicate, in a weight excess of from about 5 to about 10 times the weight of the said salt, and
   c) a sufficient amount of water to suspend the foregoing components.

2. A tasteless liquid composition for the oral ingestion of pharmacologically active agents having basic moieties initially comprising
   a) the said pharmacologically active material in the form of a salt of an inorganic acid selected from the group consisting of citric, tartaric, malic, fumaric and succinic acids,
   b) magnesium oxide or hydroxide in an amount equal to 1 to 1.2 equivalents of said inorganic acid,
   c) a water soluble pharmacologically acceptable organic acid in an amount equal to 1 to 1.2 equivalents of said pharmacologically active agent having basic moieties,
   d) a silicate adsorbent selected from the group consisting of magnesium silicate, calcium silicate, magnesium aluminum silicate, and magnesium trisilicate, in a weight excess of from about 5 to about 10 times the weight of the said salt, and e) a sufficient amount of water to suspend the foregoing components.

3. A tasteless liquid composition for the oral ingestion of pharmacologically active agents having basic moieties initially comprising, a) the said pharmacologically active material in basic form, b) water soluble pharmacologically acceptable organic acid selected from the group consisting of citric, tartaric, malic, fumaric and succinic acids in an amount equal to 1 to 1.2 equivalents of said pharmacologically active agent having basic moieties, b) a silicate adsorbent selected from the group consisting of magnesium silicate, calcium silicate, magnesium aluminum silicate, and magnesium trisilicate, in a weight excess of from about 5 to about 10 times the weight of the said salt, and c) a sufficient amount of water to suspend the foregoing components.

4. A method of making a tasteless liquid composition for the oral ingestion of pharmacologically active agents having basic moieties comprising the steps of a) preparing an aqueous solution of the said pharmacologically active material in the form of a salt of an inorganic acid in water, b) adding thereto magnesium oxide or hydroxide in an amount equal to 1 to 1.2 equivalents of said inorganic acid to form the basic form of said pharmacologically active material, c) adding a water soluble pharmacologically acceptable organic acid in an amount equal to 1 to 1.2 equivalents of said pharmacologically active agent having basic moieties, and d) adding a silicate adsorbent selected from the group consisting of magnesium silicate, calcium silicate, magnesium aluminum silicate, and magnesium trisilicate, in a weight excess of from about 5 to about 10 times the weight of the said salt.

5. The method of claim 4, wherein all steps are carried out at between 50° and 90° C.

6. The method of claim 5, wherein all steps are carried out at between 70° and 80° C.

7. The method of claim 4 wherein the number of equivalents of the pharmacologically active agent per unit volume in the initial solution of step a) is substantially the same as that desired in the composition formed by this method.

8. A method of making a tasteless liquid composition for the oral ingestion of pharmacologically active agents having basic moieties comprising the steps of a) preparing an aqueous solution of the said pharmacologically active material in the form of a salt of an organic acid in water, and b) adding a silicate adsorbent selected from the group consisting of magnesium silicate, calcium silicate, magnesium aluminum silicate, and magnesium trisilicate, in a weight excess of from about 5 to about 10 times the weight of the said salt.

9. The method of claim 8, wherein all steps are carried out at between 50° and 90° C.

10. The method of claim 9, wherein all steps are carried out at between 70° and 80° C.

11. The method of claim 8 wherein the number of equivalents of the pharmacologically active agent per unit volume in the initial solution of step a) is substantially the same as that desired in the composition formed by this method.

12. A method of making a tasteless liquid composition for the oral ingestion of pharmacologically active agents having basic moieties comprising the steps of a) preparing an aqueous dispersion of the said pharmacologically active material in its basic form, b) adding a water soluble pharmacologically acceptable organic acid in an amount equal to 1 to 1.2 equivalents of said pharmacologically active agent having basic moieties, and c) adding a silicate adsorbent selected from the group consisting of magnesium silicate, calcium silicate, magnesium aluminum silicate, and magnesium trisilicate, in a weight excess of from about 5 to about 10 times the weight of the said salt.

13. The method of claim 12, wherein all steps are carried out at between 50° and 90° C.

14. The method of claim 13, wherein all steps are carried out at between 70° and 80° C.

15. The method of claim 12 wherein the number of equivalents of the pharmacologically active agent per unit volume in the initial dispersion of step a) is substantially the same as that desired in the composition formed by this method.

* * * * *